(12) United States Patent
Hyde

(10) Patent No.: US 9,815,108 B2
(45) Date of Patent: Nov. 14, 2017

(54) RADIAL COMPRESSION MECHANISM WITH HEATING AND/OR COOLING

(71) Applicant: Tom Hyde, Chandler, AZ (US)

(72) Inventor: Tom Hyde, Chandler, AZ (US)

( * ) Notice: Subject to any disclaimer, the term of this patent is extended or adjusted under 35 U.S.C. 154(b) by 0 days.

(21) Appl. No.: 15/179,791

(22) Filed: Jun. 10, 2016

(65) Prior Publication Data
US 2017/0066040 A1    Mar. 9, 2017

Related U.S. Application Data

(60) Provisional application No. 62/174,753, filed on Jun. 12, 2015.

(51) Int. Cl.
| | |
|---|---|
| *B21D 37/16* | (2006.01) |
| *B21J 9/06* | (2006.01) |
| *B21D 26/055* | (2011.01) |
| *B21J 9/02* | (2006.01) |
| *A61F 2/95* | (2013.01) |
| *A61F 2/958* | (2013.01) |

(52) U.S. Cl.
CPC ................ *B21J 9/06* (2013.01); *A61F 2/95* (2013.01); *B21D 26/055* (2013.01); *B21D 37/16* (2013.01); *B21J 9/02* (2013.01); *A61F 2/958* (2013.01); *A61F 2002/9522* (2013.01)

(58) Field of Classification Search
CPC ........ B21J 9/06; B21J 5/00; B21J 9/02; A61F 2/95; A61F 2/958; A61F 2002/9522; B21D 37/16; B21D 26/055

USPC ....................................................... 72/342.3
See application file for complete search history.

(56) References Cited

U.S. PATENT DOCUMENTS

| | | | | |
|---|---|---|---|---|
| 3,668,917 A | * | 6/1972 | Komatsu | B21J 5/00 148/580 |
| 4,584,860 A | * | 4/1986 | Leonard | B21D 26/055 72/342.92 |
| 6,367,304 B1 | * | 4/2002 | Fahrenbach | B21J 9/02 72/342.2 |
| 8,291,570 B2 | * | 10/2012 | Eidenschink | A61F 2/95 29/283.5 |
| 2008/0072653 A1 | * | 3/2008 | Gillick | A61F 2/95 72/402 |

* cited by examiner

*Primary Examiner* — David B Jones
(74) *Attorney, Agent, or Firm* — Parsons & Goltry; Robert A. Parsons; Michael W. Goltry

(57) ABSTRACT

A radial compression mechanism includes a plurality of die, each of the plurality of die have a wedge shaped tip. The dies are arranged around a common central axis so that the wedge shaped tips form an elongated central cavity and move between an expanded position and a contracted position. Each die includes a fluid duct extending lengthwise through the die proximate the wedge-shaped tip. Each fluid duct includes an inlet fluid port and an outlet fluid port. The fluid ducts are connected in parallel by a fluid supply manifold connected to each inlet fluid port of each die by an inlet conduit, and a fluid return manifold connected to each outlet fluid port of each die by an outlet conduit.

15 Claims, 5 Drawing Sheets

RADIAL COMPRESSION MECHANISM WITH HEATING AND/OR COOLING

CROSS REFERENCE TO RELATED APPLICATION

This application claims the benefit of U.S. Provisional Patent Application No. 62/174,753, filed 12 Jun. 2015.

FIELD OF THE INVENTION

This invention relates to radial compression mechanisms and more specifically to mechanisms for compressing devices such as stents, catheters, balloons, and the like.

BACKGROUND OF THE INVENTION

In the manufacture and testing of medical devices, radial compression mechanisms are used to radially compress cylindrical devices such as stents, balloons, and catheters. For example, installation of a metal stent onto a catheter balloon is typically done by compressing the stent radially inward onto the balloon with enough pressure to permanently deform the stent to a smaller diameter and to slightly embed the metal stent into the plastic balloon. Further, a polymer stent can be installed onto a catheter balloon or a drug-coated stent (metallic or polymer) can be installed onto a catheter balloon by similar means as for a metallic stent. In a further example, a polymer catheter balloon is compressed radially after pleating to wrap the balloon tightly around the catheter shaft.

It is most often desirable to perform the compression process at a temperature above ambient, and furthermore to perform the compression process at some specific and well-controlled temperature. For example, the embedment of a compressed metallic stent into a catheter balloon, and therefore the stent's dislodgement force, can be improved if the balloon polymer is at an elevated temperature, because the balloon material is more deformable at the elevated temperature. Similarly, a polymer stent can be more reliably compressed onto a catheter balloon at elevated temperatures due to improved deformability of the stent material. In another example, the drug coating on a drug-eluting stent is rendered more compliant with elevated temperature, reducing risk of the coating cracking or delaminating from the stent when being crimped onto a balloon. In a further example, a polymer catheter balloon may be more tightly wrapped around a catheter shaft, with a smaller final diameter, after pleating if the compression is performed at elevated temperature.

Control of the elevated temperature is also important. Too low a temperature may result in poor stent dislodgement force, too-large wrapped balloon diameter, cracking of a polymer stent, or flaking of the drug coating on a drug-eluting stent during the compression process. Too high a temperature can cause damage to the elements (balloon, polymer stent, or a metallic stent may be over-compressed into its polymer balloon, or the drug compound in a drug-eluting coating on a stent or balloon may be damaged. Temperature uniformity along the length of each die and from die-to-die within the mechanism is also important. Products being crimped or compressed may require a narrow variance from the temperature setpoint, at any position along the product's length or circumference, to achieve acceptable quality.

One prior art device includes, for example, a radial compression mechanism wherein several wedge-shaped stainless steel or nickel alloy dies with planar surfaces are arranged around a common central axis to form a polygonal central cavity, the wedges being constrained and driven by a mechanism to control the size of the polygonal cavity. Prior art includes any of several types of radial compression mechanisms: such as the "hinged wedge" (U.S. Pat. No. 7,886,661); J-Crimp (U.S. Pat. No. 7,963,142); Twin-Cam (U.S. Pat. No. 8,245,559); and "Linear-motion Wedge" (U.S. Pat. No. 6,651,478), and U.S. Pat. Nos. 7,918,252, 7,407,377, 7,248,401, 7,308,748, and others.

In one example of prior art, each die of one of the above mechanism types is equipped with one or more electrically-driven heater elements to add thermal energy to heat the die, and at least one die is equipped with a temperature sensor (such as a thermocouple or RTD) to provide temperature feedback. This type of prior art is by far the most common, and is embodied by nearly all of the stent crimping and balloon wrapping machines sold. The most common material for catheter balloons is nylon, which has a glass transition temperature of about 45 to 50 deg. C. The die temperature for balloon wrapping or stent crimping of nylon balloons is typically in the range of 50 to 70 deg. C., in order to exceed the glass transition temperature and permanently deform the plastic. To allow processing of other materials, these mechanisms are typically controlled to temperatures ranging from 30 to 100 deg. C.

In another example of prior art, one of the above mechanism types is enclosed in a heated and temperature controlled chamber similar to an oven.

A shortcoming of the prior art is that it is impractical to cool the dies from some high temperature while maintaining the product under compression, because the cooling is much too slow. The control is one-sided, that is, there is no active cooling. Heat loss from the dies occurs only as small conduction losses at the mechanism interfaces and convective losses to the surrounding environment. In many applications, it is desirable to perform the compression process with the dies hot, then cool the dies to some significantly lower temperature with the product still under compression. In a typical stent-delivery balloon catheter, a metallic stent crimped onto a balloon catheter will exhibit reduced 'rebound' of the compressed balloon if it is cooled below the balloon's glass transition temperature prior to release from compression. In another example, wrapped and compressed catheter balloons typically "loosen" or "un fold" slightly upon relief of the compression and prior to cooling below the glass transition temperature. In-situ cooling of the balloon while under compression reduces this loosening. Without active cooling, this in-situ cooling takes a prohibitively long time, being therefore not productive.

Another shortcoming of the prior art results from the choice of the number of temperature sensors (one in the entire mechanism, one per die, or some distribution in between). A single temperature sensor is actually sensing only one die. Variations in individual die heat and variations in individual die heat loss results in temperature differences within the non-sensed dies compared to the controlled (sensed) die. Multiple temperature sensors within the die set have the effect of greatly increasing the complexity of control, as each sensor requires an independent control loop device.

A further shortcoming of this prior art mechanism is a lack of within-die temperature uniformity caused by a combination of localized heat input zones (the electrical heaters) and relatively poor thermal conductivity of the die material.

It would be highly advantageous, therefore, to remedy the foregoing and other deficiencies inherent in the prior art.

Accordingly it is an object of the present invention to provide new and improved radial compression mechanism. Another object of the present invention is to provide new and improved radial compression mechanism for compressing stents, catheters, balloons, polymer stents, drug-eluting stents, drug-eluting balloons, and the like in the medical device industry.

Another object of the present invention is to provide new and improved radial compression mechanism using actively-cooled and actively-heated dies to rapidly change die set temperatures.

Another object of the present invention is to provide new and improved radial compression mechanism using fluid forced-convection heat transfer in internal die ducts to effect rapid die heating and cooling.

Another object of the present invention is to provide new and improved radial compression mechanism with improved temperature control and uniformity within-die and within-mechanism.

SUMMARY OF THE INVENTION

Briefly, to achieve the desired objects and advantages of the instant invention, provided is a radial compression mechanism. The radial compression mechanism includes a plurality of die. Each of the plurality of die has a wedge shaped tip. The dies are arranged around a common central axis so that the wedge shaped tips form an elongated central cavity and are movable between an expanded position and a contracted position. Each die includes a fluid duct extending lengthwise through the die proximate the wedge-shaped tip. Each fluid duct includes an inlet fluid port and an outlet fluid port. A hot fluid supply and a cold fluid supply are selectively coupled to the inlet fluid port of each die.

In a specific aspect, the fluid ducts are connected in parallel by a fluid supply manifold connected to each inlet fluid port of each die by an inlet conduit, and a fluid return manifold connected to each outlet fluid port of each die by an outlet conduit.

BRIEF DESCRIPTION OF THE DRAWINGS

The foregoing and further and more specific objects and advantages of the invention will become readily apparent to those skilled in the art from the following detailed description of a preferred embodiment thereof, taken in conjunction with the drawings in which.

DETAILED DESCRIPTION OF THE DRAWINGS

Figure 1:
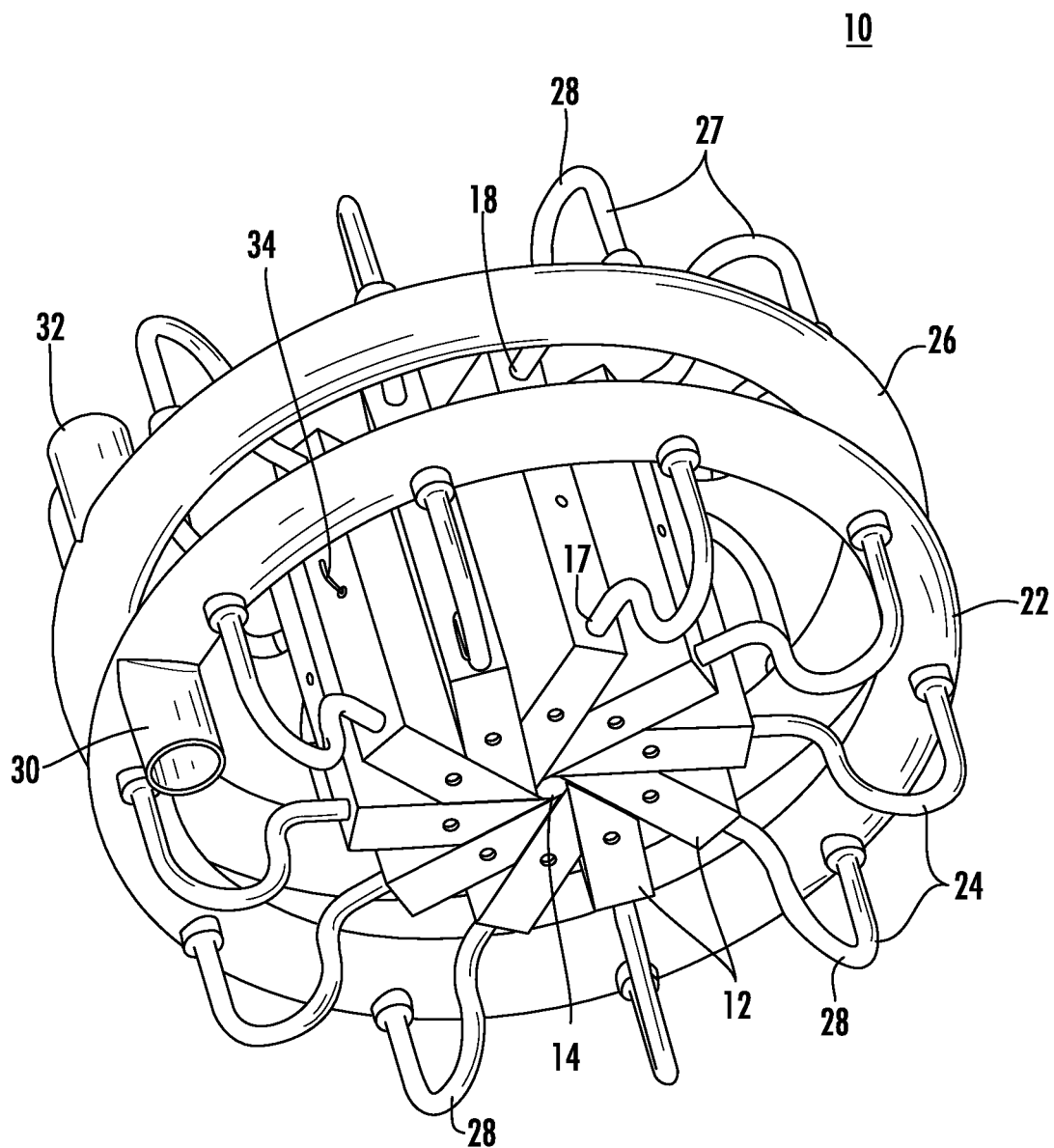
FIG. 1 is a portion of an exemplary compression mechanism in accordance with the present invention.

Turning now to the drawings, attention is directed to FIG. 1 which illustrates a portion of an exemplary compression mechanism, generally designated 10, in accordance with the present invention. Compression mechanism 10 includes a plurality of wedge-shaped die, each designated 12, arranged around a common central axis to form an elongated central cavity 14 having a roughly round cross-section. While each die 12 is preferably wedge-shaped, other shapes, as disclosed in the art, are possible. Regardless of the shape of die 12, each die 12 has a wedge shaped tip 19. Wedge shaped tips 19 of the plurality of die define elongated central cavity 14. Die 12 are movable between an expanded position and a contracted position, expanding and contacting a diameter of central cavity 14, respectively. Various apparatus for constraining and driving die 12, to control the size of central cavity 14, are known in the art and will not be illustrated or elaborated upon for simplicity and better understanding of the invention. In the present example ten wedge-shaped die 12 are included, all of which are similar.

Figure 2:
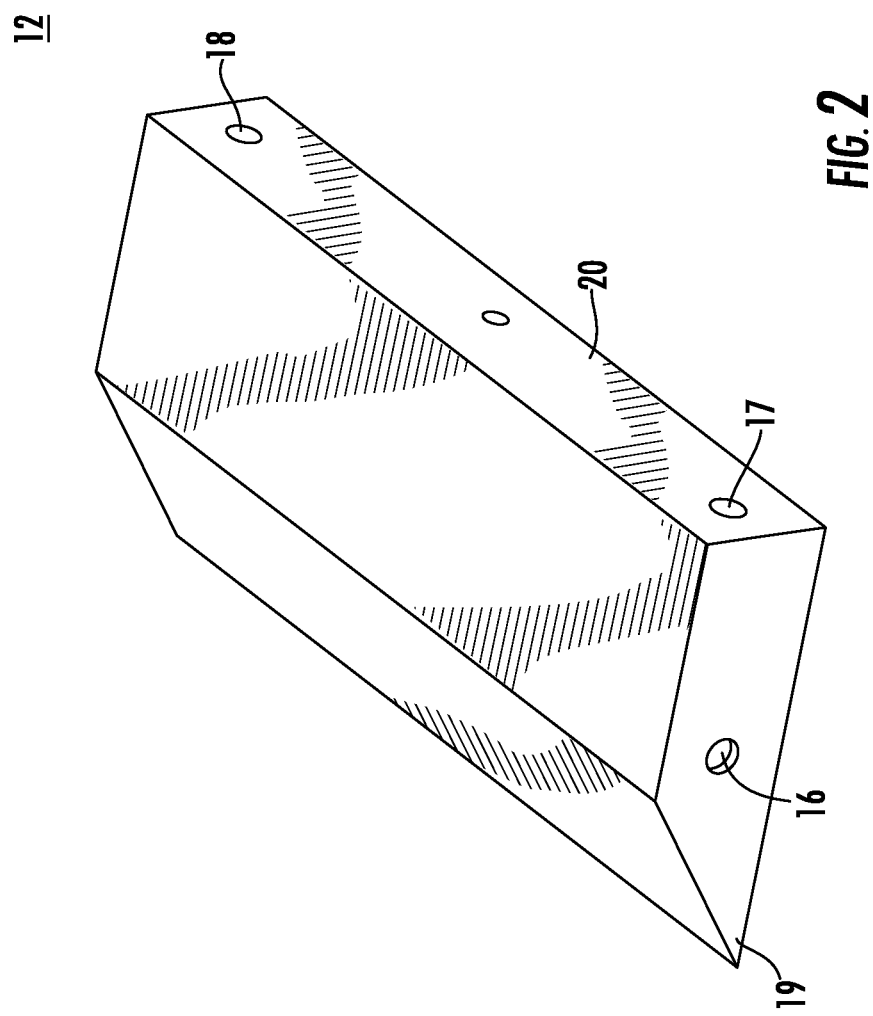
FIG. 2 is a perspective view of a single die from the mechanism of FIG. 1.

A specific example of a wedge-shaped die 12 is illustrated in an enlarged view in FIG. 2. A fluid duct 16 (illustrated in phantom) extends lengthwise through die 12 near or adjacent wedge-shaped tip 19, which forms a portion of central cavity 14 as can be seen in FIG. 1. Inlet/outlet fluid port ducts 17 and 18 extend from a heel or back surface 20 of wedge-shaped die 12 into fluid communication with fluid duct 16 adjacent opposite ends. As will be understood, die 12 is relatively easy to manufacture since it is formed as a single piece and the ducts can be formed by simply drilling horizontally therethrough. The open ends of fluid duct 16 are sealed to prevent external leakage of fluid. Die 12 construction preferably is from metal alloys having significantly higher thermal conductivity than the metals commonly used in the prior art, including but not limited to alloys such as beryllium-copper or chromium-copper. This construction results in faster within-die heat transfer and subsequently improved within-die temperature uniformity.

Referring again to FIG. 1, all of fluid ducts 16 of wedge-shaped dies 12 are connected in parallel, in this example, by connecting port duct 17 of each wedge-shaped die 12 to a manifold 22 by a conduit 24 and port duct 18 of each wedge-shaped die 12 to a manifold 26 by a conduit 27. Each conduit 24 and 27 have at least a flexible portion 28 designed to allow unhampered radial opening and closing movements of wedge-shaped dies 12 and are of the same length to insure equal fluid distribution and flow rate. The parallel connection provides essentially equal fluid flow rate in each die 12. With each die 12 connected for parallel fluid flow from a common supply at therefore a common temperature, and assuming die 12 heat losses (or gains) from the environment are small relative to the fluid heat transfer capacity of each die 12, temperature uniformity of dies 12 from die-to-die is improved over the prior art.

One of manifolds 22 and 26 is a fluid supply manifold and the other is a fluid return manifold. The supply manifold (e.g. manifold 22) is in turn connected by a conduit 30 and through appropriate conventional valves to both a hot fluid supply and a cold fluid supply. The return manifold (e.g. manifold 26) collects the fluid exiting from each die, through conduit 32, for discard or recycle. One (or more) die 12 of compression mechanism 10 is equipped with a temperature sensing element, herein designated 34 (not visible because it is embedded in the one die 12) such as an RTD, thermocouple, or thermistor. Each fluid supply at die 12 is pressurized and regulated to a temperature higher (or lower in the case of the cold supply) than the desired process temperature by a range of 1 to 25 degrees Fahrenheit or more to provide the temperature and pressure differentials necessary for heat transfer.

Die duct size (flow area), fluid heat transfer properties, fluid capacity, and fluid mass flow rate are selected such that the in-duct Reynold's number is in the fully turbulent range, and that the fluid temperature difference from inlet to outlet of each die 12 is small in the limit case of highest temperature difference between die and fluid. This results in a high heat transfer coefficient between the fluid and each die 12, enabling rapid heat exchange between fluid flowing in fluid duct 16 and die 12 with uniformity over the length of fluid duct 16.

Figure 3:
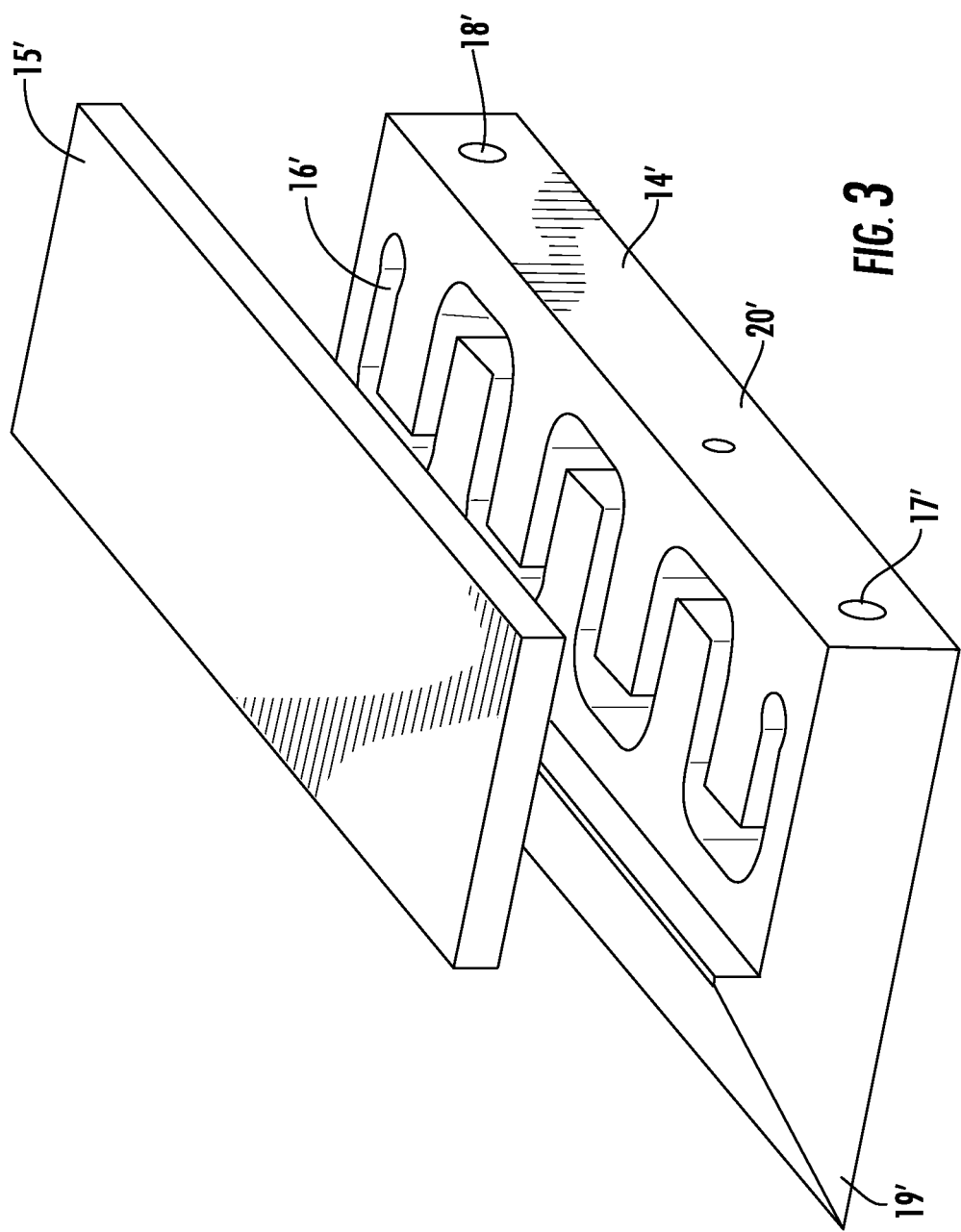
FIG. 3 is a two-piece die with sinuated fluid passage, in accordance with the present invention.

Referring now to FIG. 3, another example of a wedge-shaped die, designated 12' to indicate the different structure, is illustrated in accordance with the present invention. Wedge-shaped die 12' is a two-piece die with sinuated fluid duct or passage 16'. To make sinuated fluid passage 16' producible, wedge-shaped die 12' is manufactured in two pieces, a lower or base piece 14' including a wedge-shaped tip 19' and a cover piece 15'. With cover piece 15' removed (as illustrated in FIG. 3, sinuated fluid duct 16' can be easily milled into base piece 14'. Port ducts 17' and 18' can then be drilled from a heel 20' of base piece 14' into fluid communication with sinuated fluid duct 16'. It will be understood that forming the fluid duct in a sinuated configuration lengthens the duct and provides more thermal transference between the fluid flowing in the duct and die 12'. Straight fluid duct 12 and sinuated fluid duct 12' are simply two examples of ducts and it should be understood that many other configurations may be devised. One potential alternate is to form separate temperature transfer ducts (straight, sinuous, etc.) and attach the separate ducts externally to the crimping dies by means that effect good heat transfer. Also, while both specific examples illustrate an input at one end and an output at the other end it will be understood that an input/output duct could be coupled to the main fluid duct 16/16' at or near a central point and both ends could be coupled to the output/input duct. This configuration is especially useful for good axial temperature uniformity when dies are very long.

Figure 4:
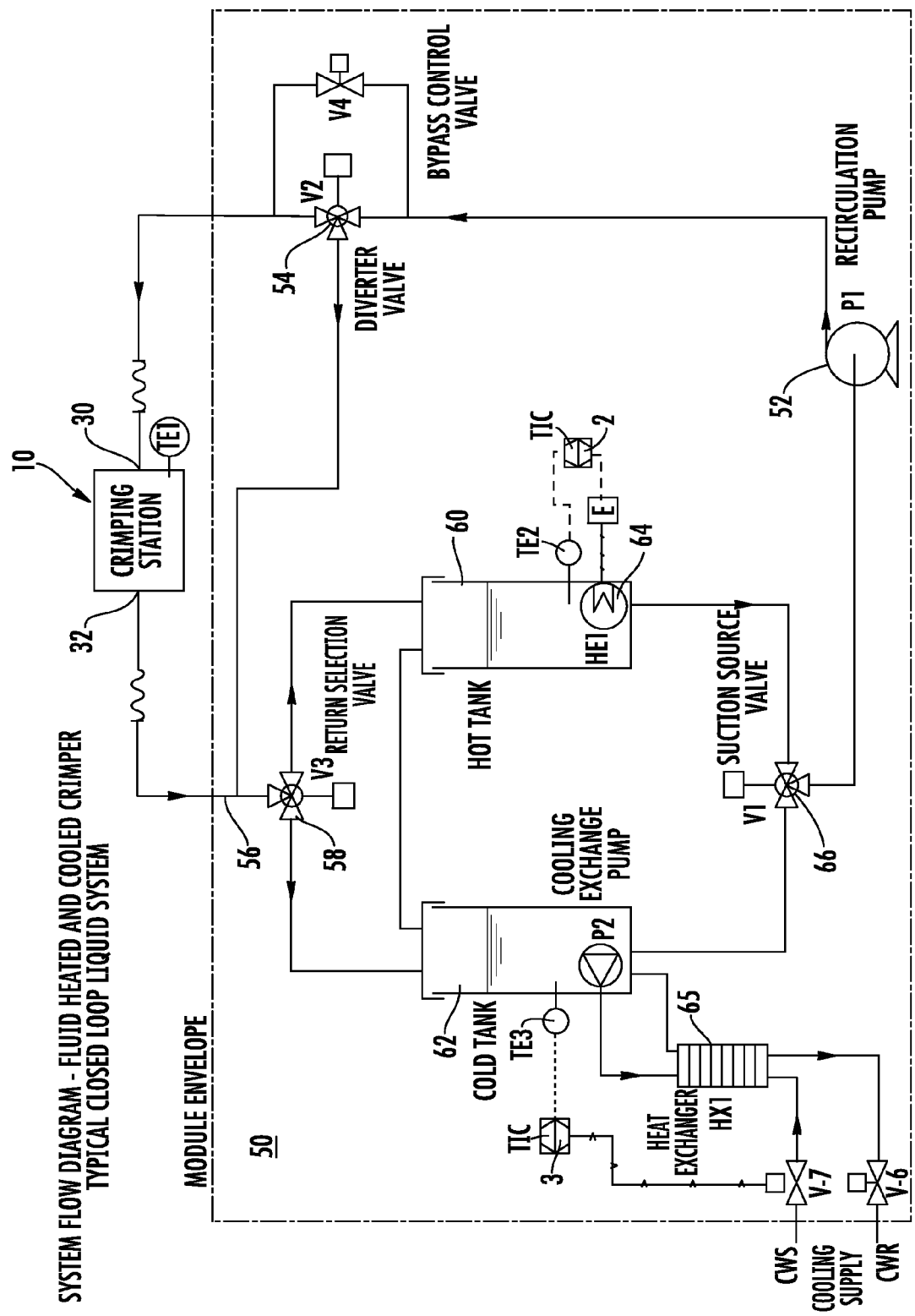
FIG. 4 is a an example of a system flow diagram illustrating a fluid heated and cooled crimper closed-loop liquid system.

Referring now to FIG. 4, an example of a system flow diagram illustrating a fluid heated and cooled crimper closed-loop liquid system 50 is illustrated. System 50 is included within a 'module envelope' represented by a dashed line. In this example, compression mechanism 10 is represented by a crimping station block, designated 10 for consistency, and conduit 30 is the fluid input or supply with conduit 32 being the return. System 50 includes a recirculation pump 52, which may be any well-known type of fluid pump, including electrical hydraulic, etc. Also, while it will be understood that water or a mixture of water is the most convenient and efficient fluid, other fluids (e.g. gas or liquid vapor) may be used in specific applications. Alternate fluids may be used to achieve a higher, lower, or both temperature capability.

The fluid output of pump 52 is supplied to conduit 30 of compression mechanism 10 through a diverter valve 54 included for normal control of fluid flow. When operated (i.e. not straight thru), diverter valve 54 directs fluid flow from conduit 30 back into a return conduit 56. Return conduit 56 is connected to conduit 32 of compression mechanism 10 and to a return selection valve 58. Return selection valve 58 is connected to one of a hot fluid tank 60 and a cold fluid tank 62 and is controlled generally by the withdrawal of fluid from either or both hot fluid tank 60 and cold fluid tank 62. The temperature of the fluid in hot fluid tank 60 is maintained at a desired temperature by a heating element 64 (including various sensors and controls). The temperature of the fluid in cold fluid tank 62 is maintained at a desired temperature, in this specific example, by means of a heat exchanger 65 coupled to a cold fluid source input and cold fluid return output through valves controlled by sensors in cold fluid tank 62.

Fluid is drawn from either or both hot fluid tank 60 and cold fluid tank 62 through a suction source valve 66, which supplies the fluid directly to the input of recirculation pump 52. Suction source valve 66 is controlled generally in response to temperature sensing element 34 and to temperatures required by specific crimping programs being operated and generally determines the temperature of the dies 12 and mode of operation (i.e. heating, cooling, etc.). Thus, hot and/or cold fluid is circulated through crimping dies 12/12' in compression mechanism 10 in accordance with the specific crimping application or operation being performed.

In one specific example of operation, with compression dies 12 hot, rapid cooling is accomplished by switching the suction source valve 66 from hot tank 60 to cold fluid tank 62. As compression die temperature, measured by temperature sensing element 34, approaches the desired cold process value, valve 66 is modulated to provide control. In a similar fashion, heating from a cold starting point is accomplished.

Figure 5:
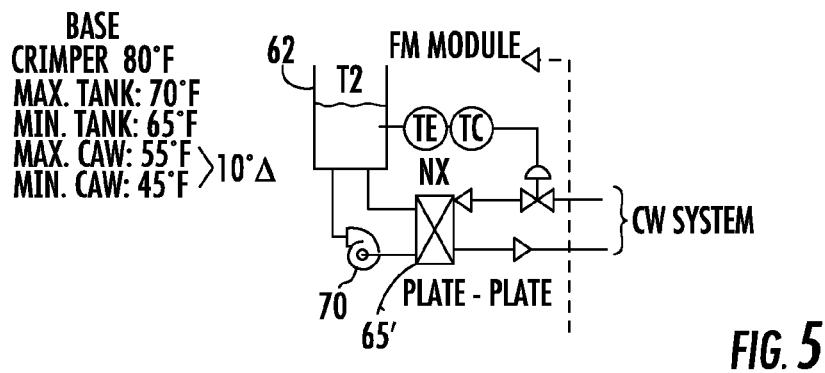
FIG. 5 illustrates an example of a closed loop cooling system, external cold water supply.
Figure 6:
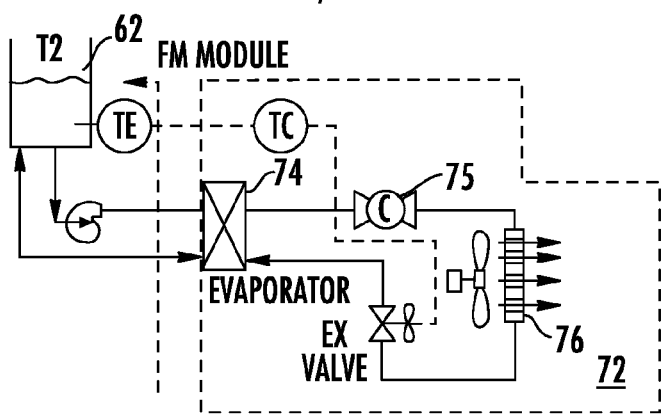
FIG. 6 illustrates an example of a closed loop cooling system with an auxiliary chiller open-loop supply.
Figure 7:
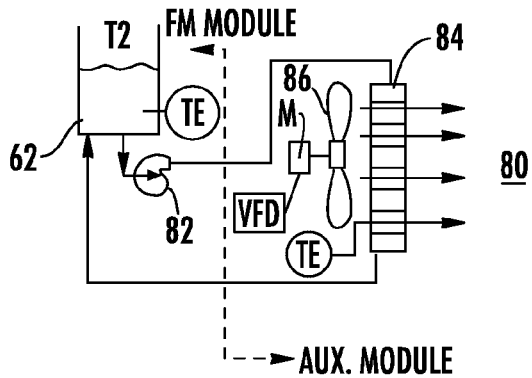
FIG. 7 illustrates an example of a closed loop cooling system with a fin tube to air auxiliary module.

Some examples of alternative apparatus for supplying cold fluid to cold tank 62 are illustrated in FIGS. 5, 6, and 7. In the example illustrated in FIG. 5, a fluid pump 70 (which may be submersible and positioned in cold tank 62) is included to enhance movement of fluid into and out of cold tank 62 from a heat exchanger 65'. This specific example allows lower cold fluids or temperatures and, therefore, faster cooling because of the forced exchange of cold fluids into cold tank 62. As an example of temperatures that may be used, if the temperature of the dies in compression mechanism 10 is selected at 80° F., maximum tank temperature is 70° F., minimum tank temperature is 65° F., maximum cold fluid supplied to the tank is 55° F., and minimum cold fluid supplied to the tank is 45° F., or 10° F. differential.

Referring to FIG. 6, an auxiliary chiller open loop system 72 is illustrated. In this system the fluid flows from cold fluid tank 62 to an evaporator 74, through a compressor 75 and into a condenser 76. The fluid then flows from the condenser 76 back to evaporator 74 and into cold fluid tank 62 to complete the closed loop. This specific example allows lower cold fluids or temperatures and, therefore, faster cooling because of the forced exchange of cold fluids into cold tank 62. As an example of temperatures that may be used, if the temperature of the dies in compression mechanism 10 is selected at 80° F., maximum tank temperature is 70° F., minimum tank temperature is 60° F., maximum cold fluid supplied to the tank is 50° F., and minimum cold fluid supplied to the tank is 40° F.

Referring to FIG. 7, an air auxiliary module 80 is illustrated. In module 80 fluid is drawn from cold fluid tank 62 by a pump 82 and flows through fin-tubes 84 that are air cooled by use of a fan 86. Module 80 results in higher base temperatures and slower cooling but does not result in condensation problems and insulation requirements, resulting in a much simpler system. As an example of temperatures that may be used, if the temperature of the dies in compression mechanism 10 is selected at 90° F., maximum tank temperature is 80° F., minimum tank temperature is 75° F.

While several examples of cooling modules have been disclosed, it will be understood that combinations of the examples may be used and many other potential systems and modules may be devised alone or in combination with the above examples.

Various changes and modifications to the embodiments herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

The invention claimed is:

1. A radial compression mechanism comprising:
    a plurality of die, each of the plurality of die having a wedge shaped tip, the plurality of die arranged around a common central axis so that the wedge shaped tips of the plurality of die form an elongated central cavity, the plurality of die movable between an expanded position and a contracted position, expanding and contacting a diameter of the central cavity, respectively;
    each die of the plurality of die include a fluid duct extending lengthwise through the die proximate the wedge-shaped tip, and each fluid duct includes an inlet fluid port and an outlet fluid port; and
    a hot fluid supply and a cold fluid supply selectively coupled to the inlet fluid port of each die.

2. A radial compression mechanism as claimed in claim 1 wherein the inlet fluid port and the outlet fluid port extend from a back surface of the die in fluid communication with the fluid duct.

3. A radial compression mechanism as claimed in claim 1 wherein the fluid ducts are connected in parallel by a fluid supply manifold connected to each inlet fluid port of each die by an inlet conduit, and a fluid return manifold connected to each outlet fluid port of each die by an outlet conduit.

4. A radial compression mechanism as claimed in claim 3 wherein each inlet conduit and each outlet conduit includes a flexible portion designed to allow unhampered movement of dies between the contracted position and the expanded position.

5. A radial compression mechanism as claimed in claim 3 wherein the supply manifold is selectively connected to the hot fluid supply and the cold fluid supply and the return manifold collects the fluid exiting from each die, for discard or recycle.

6. A radial compression mechanism as claimed in claim 1 further including at least one die carrying a temperature sensing element.

7. A radial compression mechanism as claimed in claim 1 wherein each die further comprises:
    a base piece carrying the wedge-shaped tip and having the fluid duct formed therein being non-linear; and
    a cover piece overlying the base piece.

8. A radial compression mechanism as claimed in claim 1 wherein each die is a formed as a one-piece element with a linear fluid duct.

9. A radial compression mechanism comprising:
    a plurality of die, each of the plurality of die having a wedge shaped tip, the plurality of die arranged around a common central axis so that the wedge shaped tips of the plurality of die form an elongated central cavity, the plurality of die movable between a expanded position and a contracted position, expanding and contacting a diameter of the central cavity, respectively;
    each die of the plurality of die include a fluid duct extending lengthwise through the die proximate the wedge-shaped tip, and each fluid duct includes an inlet fluid port and an outlet fluid port; and
    the fluid ducts are connected in parallel by a fluid supply manifold connected to each inlet fluid port of each die by an inlet conduit, and a fluid return manifold connected to each outlet fluid port of each die by an outlet conduit.

10. A radial compression mechanism as claimed in claim 9 wherein the inlet fluid port and the outlet fluid port extend from a back surface of the die in fluid communication with the fluid duct.

11. A radial compression mechanism as claimed in claim 9 wherein each inlet conduit and each outlet conduit includes a flexible portion designed to allow unhampered movement of dies between the contracted position and the expanded position.

12. A radial compression mechanism as claimed in claim 9 wherein the supply manifold is selectively connected to a hot fluid supply and a cold fluid supply and the return manifold collects the fluid exiting from each die, for discard or recycle.

13. A radial compression mechanism as claimed in claim 9 further including at least one die carrying a temperature sensing element.

14. A radial compression mechanism as claimed in claim 9 wherein each die further comprises:
    a base piece carrying the wedge-shaped tip and having the fluid duct formed therein; and
    a cover piece overlying the base piece.

15. A radial compression mechanism as claimed in claim 9 wherein each die is a formed as a one-piece element.

* * * * *